United States Patent [19]

Baumeister et al.

[11] Patent Number: 5,508,402
[45] Date of Patent: Apr. 16, 1996

[54] PROCESS FOR THE PREPARATION OF N,N'—SUBSTITUTED UREAS

[75] Inventors: Peter Baumeister, Flüh; Gottfried Seifert, Magden; Heinz Steiner, Münchenstein, all of Switzerland

[73] Assignee: Ciba-Geigy Corporation, Tarrytown, N.Y.

[21] Appl. No.: 451,712

[22] Filed: May 26, 1995

Related U.S. Application Data

[62] Division of Ser. No. 315,313, Sep. 29, 1994, abandoned, which is a continuation of Ser. No. 93,213, Jul. 19, 1993, abandoned, which is a continuation-in-part of Ser. No. 932,135, Aug. 18, 1992, abandoned.

[51] Int. Cl.$^6$ ............... C07D 251/46; C07D 251/52; C07D 239/69
[52] U.S. Cl. .............. 544/206; 544/208; 544/211; 544/321; 544/323; 544/332
[58] Field of Search .................... 544/205, 210, 544/213, 321, 323, 332, 206, 208, 211

[56] References Cited

U.S. PATENT DOCUMENTS 4,671,819  6/1987  Meyer .......... 71/93
4,780,125  10/1988 Meyer .......... 71/93

FOREIGN PATENT DOCUMENTS 0044210  1/1982  European Pat. Off. .
0187489  7/1986  European Pat. Off. .

OTHER PUBLICATIONS

Chem. Abst. 92:41471x (1980) (Corresponds to Kikukawa et al., Bull. Chem. Soc. JPN, 52:2609–10 (1979)) p. 741.
Chem. Abst. 85:123545v (1976) (Corresponds to JP–A–51 014 495) Itaya et al, p. 609.
Tetrahedron, vol. 37, pp. 31–36, Kikukawa et al (1981).
Synthetic Commun 20 (22), pp. 3563–3574, Zhang et al (1990).
4th IUPAC Symp. Summary. K. Oertle (Jul. 1987).
J. Org. Chem., 56, pp. 1289–1293, (1991).
Chem. Abst. 99:194410w (1983).
Heterocycles 26:7, pp. 1783–1784 (1987).
Synthetic Commun 15(13), pp. 1131–1136 (1985).
J. Org. Chem. 46, pp. 4885–4888 (1981).

*Primary Examiner*—John M. Ford
*Attorney, Agent, or Firm*—Marla J. Mathias; William A. Teoli, Jr.

[57] ABSTRACT

A process for the preparation of substituted benzenes or benzenesulfonic acid and its derivatives comprising diazotisation of an aminobenzene or ortho-amino-benzenesulfonic acid derivative followed by homogeneous palladium-catalysed coupling with an olefine and heterogeneous palladium-catalysed hydrogenation of the olefinic substituent, wherein the homogeneous catalyst is reduced and precipitated as metal after the coupling in the reaction mixture and used as a heterogeneous palladium catalyst for the hydrogenation step. The process is particular suitable for the preparation N-benzenesulfon-N'-triazinyl-urea herbicides.

30 Claims, No Drawings

PROCESS FOR THE PREPARATION OF N,N' — SUBSTITUTED UREAS

This is a divisional of Ser. No. 08/315,313, filed Sep. 29, 1994, now abandoned which is a continuation of Ser. No. 08/093,213, filed Jul. 19, 1993, now abandoned, which is a continuation-in-part of Ser. No. 07/932,135, filed Aug. 18, 1992, now abandoned.

The present invention relates to an improved process for the preparation of substituted benzenes and benzenesulfonic acid and its derivatives comprising diazotisation of an ortho-amino-benzenesulfonic acid derivative followed by homogeneous palladium-catalysed coupling and heterogeneous palladium-catalysed hydrogenation, wherein the homogeneous catalyst is reduced and precipitated as metal after the coupling and used as a heterogeneous palladium catalyst for the hydrogenation step without separation. The present invention further relates to a process for the preparation N-benzenesulfonyl-N'-triazinyl-ureas.

Benzene sulfonic acid derivatives may be used as intermediates in the production of agricultural chemicals. The preparation of N-phenylsulfonyl-N'-pyrimidinyl ureas with plant growth-regulating properties from benzene sulfonic acid salts is described, for example, in EP-A-120814.

Stepwise processes are known in which an aryl-alkene coupling catalysed by Pd(O) is followed by isolation and subsequent catalytic hydrogenation. The "Heck" reaction involves the coupling of an alkene with an arylhalide, while the "Matsuda" version of the Heck reaction proceeds via more reactive adducts e.g. an aryl diazonium ion as described, for example, in Tetrahedron Vol. 37 p. 31 to 36 (1981). Stepwise procedures are described, for example, in EP-A-120814 and by M. Somei et al. in Heterocycles, vol. 26, No. 7., p. 1783 to 1784 (1987).

Nevertheless a process for the preparation of substituted benzenesulfonic acid and its derivatives in which separation of the palladium catalyst is avoided and the palladium is used in both homogeneous and heterogeneous reaction steps is not known.

Surprisingly it has now been found that a homogeneous aryl-coupling reaction with olefines catalysed by a homogeneous palladium complex can be followed by a hydrogenation step in which the palladium from homogeneous palladium complex is used for the heterogeneous hydrogenation step as Pd metal, after which the palladium may be recovered by filtration and refined by known procedures to regenerate for example the starting complex.

It is therefore an object of the invention to provide an elegant double use of the palladium catalyst and to provide a more economic process in which a soluble palladium catalyst is used in the Matsuda homogeneous step and then used in the heterogeneous hydrogenation step.

One object of the invention is a process for the preparation of compounds of the formula Ia $$Ar—CHR_a—CHR_bR_c \quad \text{(Ia)},$$

wherein $R_a$, $R_b$ and $R_c$ are independently of each other H or a hydrogenation stable substituent and Ar means $C_6$–$C_{20}$aryl or $C_3$–$C_{20}$heteroaryl having 1 to 6 heteroatoms from the group of O, S and N, the aryl and heteroaryl being unsubstituted or substituted by hydrogenation stable residues, by a) in a first step reacting 1 mole equivalent of a compound of the formula II $$Ar—N_2^\ominus \quad \text{(IIa)}$$

with at least 1 mole equivalent of a compound of formula IIIa $$CHR_a=CR_bR_c \quad \text{(IIIa)},$$

optionally in the presence of an inert solvent, and in the presence of a catalytic amount of a homogeneous palladium catalyst and a base selected from alkali metal salts, alkaline earth metal salts and a tertiary ammonium salt of a carboxylic acid to give a compound of the formula IVa $$Ar—CR_a=CR_bR_c \quad \text{(IVa)},$$

and b) hydrogenating in a second step the compound of the formula IVa optionally in the presence of an inert solvent and in the presence of catalytic amounts of a palladium hydrogenation catalyst, characterised in that the homogeneous palladium catalyst is reduced to insoluble palladium metal in the step a) reaction mixture, which is subsequently used as the heterogeneous hydrogenation catalyst.

A preferred variant of the process according to the invention is characterised in that the heterogeneous palladium hydrogenation catalyst is formed in situ from the homogeneous palladium catalyst in the obtained step a) reaction mixture in starting the hydrogenation by introducing hydrogen.

It is very preferred to add a palladium support material for the heterogeneous hydrogenation catalyst.

The Matsuda version of the Heck reaction works in a wide scope with compounds of the formula Ia so that substituents $R_a$, $R_b$ and $R_c$ may be chosen from various groups of organic residues.

$R_a$, $R_b$ and $R_c$ may be selected from H; $C_1$–$C_{20}$alkyl; $C_1$–$C_{20}$nitriloalkyl; $C_1$–$C_{20}$hydroxyalkyl; $C_1$–$C_{20}$halogenalkyl, halogen being preferably F, Cl or Br, $C_1$–$C_{12}$alkyl-COOR$_d$, $C_1$–$C_{12}$alkyl-CO-NR$_e$R$_f$, $C_1$–$C_{12}$alkyl-SO$_2$OR$_d$ or $C_1$–$C_{12}$alkyl-SO$_2$NR$_e$R$_f$, wherein $R_d$, $R_e$ and $R_f$ independently are H, $C_1$–$C_{12}$alkyl, phenyl, benzyl or cyclohexyl; $C_1$–$C_{20}$alkyl-CO; $C_1$–$C_{20}$alkoxy; $C_1$–$C_{20}$nitriloalkoxy; $C_1$–$C_{20}$halogenalkoxy, halogen being preferably F, Cl or Br; $C_1$–$C_{20}$alkylthio; $C_1$–$C_{20}$halogenalkylthio, halogen being preferably F, Cl or Br; —SO$_2$OR$_d$, —SO$_2$—NR$_e$R$_f$, —COOR$_d$ or —CO—NR$_e$R$_f$, wherein $R_d$, $R_e$ and $R_f$ have the above meanings; halogen which is preferably F, Cl or Br; —CN; —NR$_e$R$_f$, wherein $R_e$ and $R_f$ have the above meanings; phenyl or benzyl which is unsubstituted or substituted by $C_1$–$C_{20}$alkyl; $C_1$–$C_{20}$nitriloalkyl; $C_1$–$C_{20}$hydroxyalkyl; $C_1$–$C_{20}$halogenalkyl, halogen being preferably F, Cl or Br; $C_1$–$C_{12}$alkyl-COOR$_d$, $C_1$–$C_{12}$alkyl-CO-NR$_e$R$_f$, $C_1$–$C_{12}$alkyl-SO$_2$OR$_d$ or $C_1$–$C_{12}$alkyl-SO$_2$-NR$_e$R$_f$, wherein $R_d$, $R_e$ and $R_f$ independently are H, $C_1$–$C_{12}$alkyl, phenyl, benzyl or cyclohexyl; $C_1$–$C_{20}$alkyl-CO—; $C_1$–$C_{20}$alkoxy; $C_1$–$C_{20}$nitriloalkoxy; $C_1$–$C_{20}$halogenalkoxy, halogen being preferably F, Cl or Br; $C_1$–$C_{20}$alkylthio; $C_1$–$C_{20}$halogenalkylthio, halogen being preferably F, Cl or Br; —SO$_2$OR$_d$, —SO$_2$—NR$_e$R$_f$, —COOR$_d$ or —CO—NR$_e$R$_f$, wherein $R_d$, $R_e$ and $R_f$ have the above meanings; halogen which is preferably F, Cl or Br; —CN; —NR$_e$R$_f$, wherein $R_e$ and $R_f$ have the above meanings. $R_d$ may also represent —OM or —O(M$_1$)$_{1/2}$, where M is an alkali metal atom or a tertiary ammonium group, having from 3 to 18 carbon atoms, and M$_1$ is an alkaline earth metal atom. All alkyl, alkoxy and alkylthio groups contain preferably 1 to 12 carbon atoms, more preferably 1 to 8 carbon atoms and most preferably 1 to 4 carbon atoms.

Ar as aryl contains preferably 6 to 16, more preferably 6 to 12 carbon atoms and Ar may be monocyclic or condensed polycyclic aryl, whereby the polycyclic aryl may contain up to 5 and preferably up to 3 rings. Preferred Ar-groups are naphthyl and especially phenyl. The heteroaryl contains preferably 3 to 14, more preferably 3 to 10 carbon atoms, having preferably 1 to 4 and more preferably 1 to 3 heteroatoms from the group of O, S and N, whereby N is especially preferred. The heteroaryl may be monocyclic or condensed polycyclic heteroaryl, whereby the polycyclic heteroaryl may contain up to 5 and preferably up to 3 rings. Preferred heteroaryl is pyridine, triazine, pyrimydine and chinoline.

The aryl and heteroaryl may be substituted independently by the groups as mentioned above for $R_a$, $R_b$ and $R_c$ and also by —OH or —SH.

The reaction conditions may vary in broad range but may be preferably selected as for the more preferred object described below.

A more preferred object of the invention is a process for the preparation of compounds of the formula I

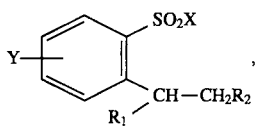

wherein X represents hydroxyl, —OM, —O($M_1$)$_\frac{1}{2}$ or $NH_2$, where M is an alkali metal atom or a tertiary ammonium group, having from 3 to 18 carbon atoms, and $M_1$ is an alkaline earth metal atom, Y is H, Cl, F or Br, $R_1$ is H, F, Cl, Br or —$COOR_3$, $R_2$ is —COO($C_1$–$C_4$-alkyl), —(CO)$R_3$ or $C_1$–$C_2$-alkyl which is unsubstituted or substituted by halogen atoms, and $R_3$ is H or $C_1$–$C_4$-alkyl, by a) in a first step reacting 1 mole equivalent of a compound of the formula II

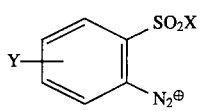

with at least 1 mole equivalent of a compound of formula III

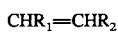

optionally in the presence of an inert solvent, and in the presence of a catalytic amount of a homogeneous palladium catalyst and a base selected from alkali metal salts, alkaline earth metal salts and a tertiary ammonium salt of a carboxylic acid to give a compound of the formula IV

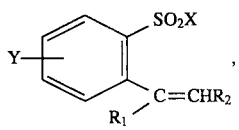

and b) hydrogenating in a second step the compound of the formula IV optionally in the presence of an inert solvent and in the presence of catalytic amounts of a hydrogenation catalyst, characterised in that the homogeneous palladium catalyst is reduced to insoluble palladium metal in the step a) reaction mixture, which is subsequently used as the heterogeneous hydrogenation catalyst.

A preferred variant of this process is characterised in that the heterogeneous palladium hydrogenation catalyst is formed in situ from the homogeneous palladium catalyst in the obtained step a) reaction mixture in starting the hydrogenation by introducing hydrogen.

It is very preferred to add a palladium support material for the heterogeneous hydrogenation catalyst.

M in the above definition is preferably lithium, sodium or potassium. $M_1$ is preferably magnesium or calcium. $M_1$ as tertiary ammonium may be represented by the formula $R_4R_5R_6NH^+$, wherein $R_4$, $R_5$ and $R_6$ independently are $C_1$–$C_6$-alkyl, preferably $C_1$–$C_4$-alkyl, or $R_4$ and $R_6$ together are —(CH$_2$)$_4$—, —(CH$_2$)$_5$— or —(CH$_2$)$_2$O(CH$_2$)$_2$— and $R_6$ is $C_1$–$C_6$-alkyl, preferably $C_1$–$C_4$-alkyl. Some examples for alkyl are methyl, ethyl, n- or i-propyl, n-, i- or t-butyl.

In the above definition alkyl denotes straight chain or branched alkyl, e.g. methyl, ethyl, n-propyl, isopropyl, and the four isomers of butyl.

The halogen substituent for $R_2$ as $C_1$–$C_2$-alkyl is preferably F or Cl.

$R_1$ is preferably H, and $R_2$ is preferably —$CF_3$, —$CF_2Cl$, —$CFCl_2$, —$CCl_3$, —COO($C_1$–$C_4$-alkyl) or —(CO)$CH_3$. In an especially preferred embodiment, $R_1$ is H and $R_2$ is —$CF_3$ or —(CO)$CH_3$.

X is preferably OH, ONa or OK. Y is preferably H.

The starting point of the process according to the invention is an aryl diazonium cation of formula II which may be formed by methods well documented in the literature.

The diazonium compound of formula II may be formed in situ by well-known methods, or added as a salt, in which case examples of the counter anion for the compounds of formula II are $PF_6^-$, $BF_4^-$, $OAc^-$, $HSO_4^-$, $SO_4^{2-}$, $CH_3(C_6H_4)SO_3^-$ and $CH_3SO_3^-$. The in situ formation may also be carried out in the presence of compounds of formula III, for example with the addition of alkylnitrites such as t-butyl nitrite as described in J. Org. Chem. Vol. 46, p. 4885 to 4888 (1981).

The palladium catalyst used in the first reaction step may be generated in situ or ex situ by reduction of a palladium(II) compound optionally in the presence of a salt such as sodium acetate and in the presence of suitable ligand-forming compounds. Suitable palladium compounds include $PdCl_2$, $PdBr_2$, $Pd(NO_3)_2$, $H_2PdCl_4$, $Pd(OOCCH_3)_2$, [PdCl$_4$]Na$_2$, [PdCl$_4$]Li$_2$, [PdCl$_4$]K$_2$, palladium(II)acetylacetonate, dichloro-(1,5-cyclooctadiene)palladium(II), dichlorobis-(acetonitrile)palladium(II), dichlorobis-(benzonitrile)palladium(II), π-allylpalladium(II)chloride dimer, bis-(π-methylallyl palladium(II)chloride) and π-allylpalladium(II)acetylacetonate. Suitable ligand-forming compounds are for example olefins as described by the compounds of formula III, dibenzylideneacetone (dba) unsubstituted or substituted with halogen (F, Cl and Br), $C_1$–$C_4$-alkyl or $C_1$–$C_4$-alkoxy in the benzene rings, phosphites such as those of formula P(OR$_7$) wherein R$_7$ is for example phenyl, $C_1$–$C_6$-alkyl or a partially or perfluorinated $C_1$–$C_6$-alkyl, and CO. The substituents in the benzene rings are preferably linked in the para-positions of the benzene rings. The ligand forming compounds may be used alone or in combinations of at least two compounds.

Suitable reducing agents are for example CO, H$_2$, formates, primary or secondary $C_1$–$C_8$-alkanols, hydrazine, amines and mixtures of CO with alkanols or water.

The catalyst may be added as Pd(dba)$_2$, Pd(dba)$_3$.solvent, Pd$_2$(dba)$_3$ or Pd$_2$(dba)$_3$.solvent, where the abbreviation "dba" stands for dibenzylidene acetone. The dba ligand may be unsubstituted or substituted in the aromatic part as described above.

The palladium catalyst may be used in an amount of about 0.01 to 5 mole %, based on the diazonium salt of formula II.

The base added in the first reaction step is used as a buffer to neutralise the acids present in the formation of the diazonium salts. The base may be used in at least equimolar amounts related to the diazonium compounds of formula II and preferably in an excess of up to 10 moles. Suitable bases are Li—, Na—, K—, $NH_4$—, Mg—, Ca— and $NH(C_1-C_{18}$-alkyl)$_3$-salts of carboxylic acids such as $C_1-C_4$-carboxylic acids or benzoic acid. Examples of suitable bases are lithium, potassium or sodium -acetate, -butyrate, -propionate and stearate, barium- and calcium acetate, calcium propionate and -stearate, lithium and sodium benzoate, and ammonium acetate; salts of acetic acid with triethylamine, tri-n-butylamine, tri-(2-ethylhexylamine), tri-n-octylamine and tri-n-dodecylamine. Especially preferred are alkaline metal acetates, which form acetic acid as a desirable component in the arylation step. Particularly preferred bases are sodium and potassium acetate in excess. The bases may also be used as salts in the catalyst generation described above.

A stoichiometric amount or small excess of alkene of formula III is preferred.

After the first reaction step, the homogeneous catalyst is reduced to form a heterogeneous catalyst. It is advantageous to use $H_2$ as reducing agent, since the addition of a further reactand can be avoided. It is very advantageous to add a support material for the palladium catalyst for the hydrogenation step, said support material being inert under the reaction conditions. The presence of the catalyst support or carrier can facilitate the separation of the catalyst on completion of the reaction. Examples of suitable support materials are activated carbon, carbon black, metal oxides e.g. $Al_2O_3$ and $SiO_2$, ceramics, glass and silicates e.g. synthetic and naturally occurring zeolites. Activated carbon or carbon black are preferred. The weight ratio of the catalyst support to the homogeneous palladium catalyst may be for example from 50:1 to 1:1, preferably from 20:1 to 1:1 and more preferred from 15:1 to 2:1.

The reaction temperature for the coupling step should be below the decomposition temperature of the diazonium ion, and a suitable range is between −20° and +40° C. The hydrogenation step can be carried out between room temperature and 200° C. To minimise side reactions it is advantageous to carry out the coupling step under elevated partial pressure of the coupling component of formula III, for example up to 10 bar, preferably between atmospheric pressure and 2 bar (1 bar=1×10$^5$ Pascals).

It is advantageous to carry out the hydrogenation stage of the process according to the invention at an elevated pressure, for example up to 40 bar. The hydrogen partial pressure is preferably between atmospheric pressure and 3×10$^6$ Pascals.

Solvents for the process according to the invention may be, for example one of, or a mixture of at least one of the following: alcohols; ketones; carboxylic acids; sulfones; N,N-tetrasubstituted ureas; N-alkylated lactams or N-dialkylated acid amides; ethers; aliphatic, cycloaliphatic or aromatic hydrocarbons, which may be substituted with fluorine, chlorine, or $C_1-C_4$-alkyl; carboxylic acid esters and lactones; nitriles.

Some specific examples of solvents are: alcohol: methanol, ethanol, propanol, butanol, pentanol, isopropanol, hexanol, heptanol octanol, t-butylalcohol, ethyleneglycol and diethyleneglycol. ketone: acetone, methylethylketone, methylisobutylketone, cyclohexanone. carboxylic acid: ethanoic acid, propanoic acid. sulfone: dimethylsulfone, diethylsulfone, tetramethylenesulfone, sulfolan. N,N-tetrasubstituted urea: N-methylethyl-N'-methylethylurea, N,N-dimethyl-N'-dipropylurea, tetramethylurea, tetraethylurea, N,N'-dimethyl-N,N'-1,3-propyleneurea, N,N'-dimethyl-N,N'-ethyleneurea. N-alkylated lactam: N-methylpyrrolidone, N-ethylpyrrolidone. N-dialkylated acid amide: N-dimethylformamide, N-diethylformamide, N-dimethylacetamide. ether: polyethylglycolether, diethyleneglycoldimethylether, diiethyleneglycoldiethylether, tetrahydrofuran, dioxan, methyl-t-butylether, diethyleneglycolmonomethylether and ethyleneglycolmonomethylether. aliphatic hydrocarbon: methylene chloride, pentane, hexane. cycloaliphatic hydrocarbon: cyclohexane, decahydronaphthalene. aromatic hydrocarbon: xylene, tetrahydronaphthalene, dichlorobenzene. carboxylic acid ester: benzoic-methylester, ethylacetate, δ-butyrolactone, n-butylacetate. nitrile: acetonitrile, benzonitrile, phenylacetonitrile.

It may be advantageous to use an ether/water, an ether/alcohol or an alcohol/water mixture as solvent for the diazotisation. The arylation step is preferably carried out under water-free reaction conditions. Water present in the diazotisation is preferably removed by the addition of carboxylic acid anhydrides such as acetic anhydride or by other well-known methods.

A further object of the invention is the reaction procedure in an alcohol as solvent, for example pentanol or isopropanol, which is surprising in view of the observation made in Tetrahedron Vol. 37, p. 31 (1981) that the use of alcoholic solvent caused reduction of diazonium salts.

Preferred solvents are butanol, pentanol, isopropanol, acetonitrile, ethanoic acid and dioxan or mixtures of these solvents.

A preferred embodiment of the process according to the invention is that the reaction is carded out as a one-pot reaction.

The process according to the invention has the following advantages:

i) The catalytic material is used in two consecutive and different reaction steps. The homogeneous catalyst for the Matsuda reaction is converted in situ into the necessary heterogeneous hydrogenation catalyst for the next step.

ii) The catalyst is recovered by filtration at the end of the hydrogenation step.

iii) More efficient use is made of the catalytic material.

iv) The palladium catalyst may be recycled from the reaction medium with negligible loss.

v) Mild conditions are used.

vi) Purer product is obtained in a higher yield.

vii) Elegant double use of expensive palladium is achieved.

viii) The process can be carded out in alcoholic solvents.

ix) Isolation of intermediate is avoided.

x) Economic production of herbicides (sulfonyl-ureas) on an industrial scale.

It is desirable to recycle the catalyst following hydrogenation. This can be achieved by known methods.

A further object of the invention is a process for the manufacture of compounds of the formula V

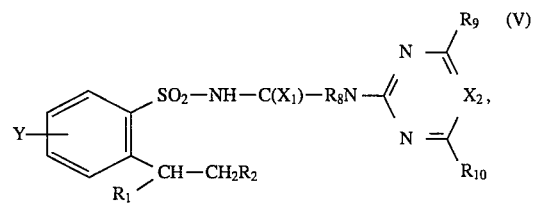

wherein $X_1$ is S or O, $X_2$ is N or CH,

Y is H, Cl, F or Br, $R_1$ is H, F, Cl, Br or —$COOR_3$, $R_2$ is —COO($C_1$–$C_4$-alkyl), —(CO)$R_3$ or $C_1$–$C_2$-alkyl which is unsubstituted or substituted by halogen atoms, and $R_3$ is H or $C_1$–$C_4$-alkyl, $R_8$ is H, $C_1$–$C_3$alkyl or $C_1$–$C_3$alkoxy $R_9$ is $C_1$–$C_3$alkyl, $C_1$–$C_3$haloalkyl, $C_1$–$C_3$alkoxy or $C_1$–$C_3$haloalkoxy, and $R_{10}$ is H, halogen, $NH_2$, NH($C_1$–$C_3$alkyl), NH($C_1$–$C_3$alkyl)$_2$, $C_1$–$C_3$alkyl, $C_1$–$C_3$haloalkyl, $C_1$–$C_3$alkoxy or $C_1$–$C_3$haloalkoxy, by a) reacting in a first step 1 mole equivalent of a compound of the formula IIb

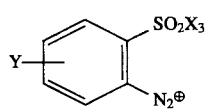

(IIb)

wherein $X_3$ represents hydroxyl, —OM or —O($M_1$)$_{1/2}$, where M is an alkali metal atom or a tertiary ammonium group, having from 3 to 18 carbon atoms, and $M_1$ is an alkaline earth metal atom, with at least 1 mole equivalent of a compound of formula IIIb

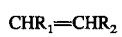

$CHR_1$=$CHR_2$ (IIIb), optionally in the presence of an inert solvent, and in the presence of a catalytic amount of a homogeneous palladium catalyst and a base selected from alkali metal salts, alkaline earth metal salts and a tertiary ammonium salt of a carboxylic acid to give a compound of the formula IVb

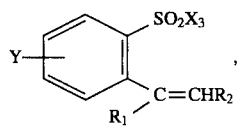

(IVb)

and b) hydrogenating in a second step the compound of the formula IVb optionally in the presence of an inert solvent and in the presence of catalytic amounts of a hydrogenation catalyst, to form a compound of the formula Ib

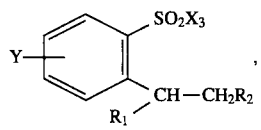

(Ib)

c) reacting in a third step the compound of formula Ib with at least 1 mole of a halogenating agent to form the sulfochloride, which is then reacted with $NH_3$ to give the sulfonamide of the formula Ic

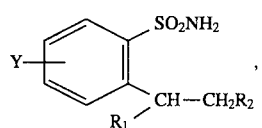

(Ic)

d) reacting the compound of the formula Ic with $COCl_2$ or $CSCl_2$ to obtain a compound of the formula VI

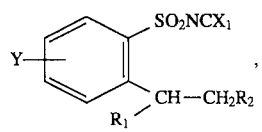

(VI), and e) reacting the compound of the formula VI with a compound of the formula VII

(VII)

to form the compound of the formula V, characterised in that the homogeneous palladium catalyst is reduced to insoluble palladium metal in the step a) reaction mixture, which is subsequently used as the heterogeneous hydrogenation catalyst.

A preferred variant of this process is characterised in that the heterogeneous palladium hydrogenation catalyst in the step b) reaction is formed in situ from the homogeneous palladium catalyst in the obtained step a) reaction mixture in starting the hydrogenation by introducing hydrogen.

It is very preferred to add prior to the start of the hydrogenation a solid palladium support material for the heterogeneous hydrogenation catalyst.

The preferred embodiments for the production of compounds of the formula I applies also in the above steps a) and b) reactions. $X_3$ preferably represents hydroxyl or a group —OM, wherein M is an alkali metal, preferably K or Na.

$X_1$ is preferably O. $X_2$ is preferably N. $R_8$ is preferably H. $R_9$ is preferably $C_1$–$C_3$alkyl, especially methyl or ethyl. $R_{10}$ is preferably $C_1$–$C_3$alkyl, especially methyl or ethyl, or $C_1$–$C_3$alkoxy, especially methoxy or ethoxy.

The process is especially used for the production of N-(4-methoxy-6-methyl- 1,3,5-triazine- 2-yl)-N'-[2-(3,3,3-trifluoroprop-1-yl)-benzenesulfonyl]-urea.

Reaction steps c), d) and e) are well known and described for example in U.S. Pat. No. 4,780,125. More preferred embodiments of these reaction steps are described below.

In the step c) reaction the preferred halogenating agent is $COCl_2$ which may be used in excess, for example 2 to 3 mole excess. The reaction may be catalyzed by the addition of N-dialkyl carboxylic acid amides like dimethylformamide, or by lactames like N-methylpyrrolidone. Catalytic amounts are for example 0.001 to 10 mole percent related to the amount of compound Ib. The reaction can be carried out under normal pressure or elevated pressure of up to 10 bar, preferably up to 5 bar. The temperature may be from 20° to 150° C., preferably 60° to 120° C. Solvents may be used as those mentioned before. Preferred are halogenated hydrocarbons, especially chlorobenzene.

The sulfochloride is preferably treated without isolation in the obtained reaction mixture with aqueous $NH_3$ in a concentration of preferably 20 to 40% at temperatures of preferably 20° to 100° C., more preferably 40° to 80° C. After cooling of the reaction mixture the compound of formula Ic precipitates and may be filtered off.

The step d) reaction is preferably carried out with an excess of phosgene or thiophosgene, for example 2 to 5 moles and preferably 2 to 3 moles. The reaction temperature is preferably 50° to 180° C. and more preferably 70° to 150° C. The reaction is preferably catalyzed by the addition of aliphatic or cycloaliphatic isocyanates having 1 to 10 carbon atoms like cyclohexylisocyanate. Catalytic amounts are for example 0.001 to 10 mole percent related to the amount of compound Ic. The reaction can be carried out under normal pressure or elevated pressure of up to 10 bar, preferably up to 5 bar. Solvents may be used as those mentioned before. Preferred are halogenated hydrocarbons, especially chlorobenzene.

The step e) reaction is preferably carried out in the presence of a solvent as those previously mentioned, especially halogenated hydrocarbons as chlorobenzene. A preferred temperature range is from 20° to 180° C., especially 50° to 150° C. The reaction is in general carried out under normal pressure or an elevated pressure of up to 1 bar. Equivalent molar ratios of the compounds of the formulae VI and VII are preferred. In a preferred embodiment the obtained reaction solution with the isocyanate of formula VI is added to the solution or suspension of the compound of the formula VII. After cooling of the reaction mixture the compound of the formula V may be filtered off and may be purified by washing the filter cake with a mineral acid like hydrochloric acid and then with an alcanol like methanol. The product is obtained in high yields (90% or more) and purity (content at least 95% and up to more than 99%). The inventive process is economic, ecologic, technically feasible and save even on an industrial scale.

The following examples illustrate the invention.

EXAMPLE 1

Preparation of Sodium Trifluoropropyl-benzenesulfonate (in isopropanol)

a) Preparation of Diazosulfonate 173.3 g aniline-2-sulfonic acid (1 mol) are stirred into 750 g isopropanol (IPA) together with 75 g water at 15° to 20° C. in a 1.5 dm$^3$ double-sleeve vessel. 89 g isopropylnitrite (IPN*) (1 mol) are added dropwise to the reaction mixture over 60 minutes while stirring is continued at between 15° and 20° C. Any unreacted IPN is consumed by the addition of dilute aniline-2-sulfonic acid. The diazo suspension obtained is cooled and stored at between 0° and 5° C.

* IPN may be made by the reaction of isopropanol with sodium nitrite and HCl at 0° C.

b) Preparation of Sodium Trifluoropropenyl-benzenesulfonate

The diazo suspension from 1a) is transferred to a pressure vessel equipped with a pressure regulator. 123 g dry sodium acetate (1.5 mol) are added and the mixture stirred for 1 hour. 3 g Pd(dba)$_2$ (0.005 tool) are added, the mixture stirred for 5 minutes and the reaction vessel closed. At 1 bar and with the temperature between 5° and 10° C. 106 g 3,3,3-trifluoropropene (1.1 mol) are introduced over a 4 hour period. After the first hour the temperature is increased to 27° to 28° C. and kept there until no more nitrogen is evolved. Approximately 25 dm$^3$ gas are evolved. The reaction mixture is transferred into a double-sleeved reaction vessel, 500 ml water added and the isopropanol is distilled off as an azeotrope isopropanol/water at atmospheric pressure. The aqueous solution containing 255 g sodium trifluoropropenyl-benzenesulfonate is cooled to room temperature.

c) Preparation of Sodium Trifluoropropyl-benzenesulfonate

The reaction mixture from 1 b) is transferred into a hydrogenation autoclave and 20 g activated carbon are added. The hydrogenation is carded out at 1 bar and 30° to 40° C. for 6 to 8 hours. The catalyst is filtered off and washed with 100 ml water. The aqueous filtrate contains 256 g of the title compound, determined by high pressure liquid chromatography. The aqueous solution of sodium trifluoropropyl-benzenesulfonate (1020 g) can be converted to the corresponding sulfonamide (1d) via the acid chloride.

d) Characterisation of the Title Compound

The title sodium salt may be characterised by conversion to the corresponding sulfonamide via the respective acid chloride.

1020 g 27% aqueous solution of sodium trifluoropropyl benzene sulfonate (1 mol) are acidified with 75 g 32% HCl to pH 1. 400 g water are evaporated off at 55° to 62° C. under 150 mbar vacuum. 1385 g chlorobenzene are added and a further 235 g water removed under 280 mbar vacuum. 15.4 ml dimethylformamide are added and the reaction mixture heated to between 100° and 105° C. The temperature remains at this level and 281 g phosgene are admitted over a 10-hour period. After 30 min stirring, the vessel is evacuated to 400 mbar and 215 ml chlorobenzene distilled off at between 90° and 105° C. The suspension is filtered at room temperature and washed with chlorobenzene. The clear brown filtrate containing the corresponding sulfochloride is warmed to between 55° and 60° C. and 155 g 30% ammonia added dropwise over a 30 min period. After stirring for a further 15 min, 4.5 g activated charcoal are added. About 106 g water are evaporated off and the dry suspension diluted with 410 ml chlorobenzene. The suspension (NH$_4$Cl) is filtered over a prewarmed suction filter treated with hyflo and the filtercake washed with 165 ml hot chlorobenzene. After crystallisation the suspension is cooled slowly to between 0° and 5° C. The suspension is stirred for 30 min and filtered. The filtercake is washed with cold chlorobenzene and dried in a vacuum chamber at 70° C. 229 g trifluoropropyl benzene sulfonamide are obtained.

EXAMPLE 2

Preparation of Sodium Trifluoropropyl-benzenesulfonate (in ethanoic acid)

a) Preparation of diazosulfonate 244.6 g 88.5% aniline-2-sulfonic acid (1.25 mol) are stirred into 900 ml dry ethanoic acid at room temperature. 85.8 g 96% sulfuric acid are run into the reaction mixture over 30 minutes while stirring is continued. The suspension is cooled to between 18° and 20° C. 215.6 g 40% aqueous sodium nitrite solution (1.25 tool) are added dropwise to the reaction mixture at between 18° and 20° C. which is stirred for a further 30 minutes. 3 ml 16.7% aqueous aniline-2-sulfonic acid are stirred in to consume any excess nitrite. Over a period of 3 hours at between 20° and 24° C., 497.5 g ethanoic anhydride (4.87 mol) are added, and after stirring for a further 1 hour, the resulting yellow suspension is cooled to between 12° and 15° C.

b) Preparation of sodium trifluoropropenyl-benzenesulfonate

The diazo suspension from 2a) is transferred to a 2.5 dm$^3$ vessel. At between 15° and 17° C. 220 g sodium acetate (2.68 mol) are added and the mixture is stirred for 1 hour. The temperature rises to 20° to 24° C. and stirring is continued for 45 minutes. With the temperature at 24° C., 3.6 g Pd(dba)$_2$ are added and the mixture stirred for 5 minutes. 130 g 3,3,3-trifluoropropene (1.35 mol) are introduced over a 4 hour period. A mildly exothermic reaction follows and the temperature remains at between 25° and 28° C. for a further 30 minutes until no more nitrogen is evolved. Approximately 34 dm$^3$ gas are evolved. The ethanoic acid is distilled off under vacuum (200 mbar) at a temperature of 70° to 90° C. When the distillation residue weight has fallen to between 850 and 900 g, 550 ml water are added and the mixture stirred at between 60° and 65° C.

c) Preparation of Sodium Trifluoropropyl-benzenesulfonate

The reaction mixture from 2b) is transferred into a hydrogenation autoclave and 35 g activated carbon are added. The hydrogenation is carried out at a pressure of 1 bar and a temperature of between 30° and 40° C. for 6 to 8 hours. The palladium-containing catalyst is separated by filtration and washed with 120 ml water; the aqueous filtrate contains 314 g of the title compound, determined by HPLC, and less than 2 ppm Pd. The aqueous solution of sodium trifluoropropyl-benzenesulfonate can be convened directly to the corresponding sulfonamide as described in 1d) or isolated as follows: The aqueous solution of sodium trifluoropropyl-benzenesulfonate is concentrated to 800 g. At 65° to 70° C. approximately 330 g 30% NaOH are added until a pH of 9 is reached, when the product precipitates. After cooling to room temperature the suspension is filtered and washed with 400 ml 25% NaCl brine in 4 portions. The wet cake is dried in a vacuum oven at 80° C. 420 g sodium trifluoropropenyl-benzenesulfonate are obtained (assay 70% determined by LC analysis).

EXAMPLE 3

Preparation of N-(4-methoxy-6-methyl-1,3,5-tiazine-2-yl)-N'-[2-(3,3,3-trifluoroprop-1-yl)-benzenesulfonyl]-urea in a pilot plant The following reactions are carried out in enamelled 630 l vessels.

a) Preparation of sodium-[2-(3,3,3-trifluoro-1-propenyl)]-benzene-sulfonate Aniline-2-sulfonic acid is diazotised with pentylnitrite (molar ratio 1:1.05) at 15° to 20° C. in pentanol containing up to 10% water as solvent. Excess pentylnitrite is destroyed with sulfamic acid and the water is convened to acetic acid by adding acetic acid anhydride. Sodium acetate (molar ratio aniline-2-sulfonic acid to sodium acetate 1:2) is added and stirring is continued for 90 minutes at 20° to 30° C. In a separate stainless steel vessel, dibenzylideneacetone (molar ratio diazonium salt to dibenzylideneacetone 1:0.04) and sodium acetate (molar ratio diazonium salt to sodium acetate 1:0.1) are mixed in pentanole and a solution of palladium dichloride (molar ratio diazonium salt to palladium dichloride 1:0.01) is added at 60° C. After cooling to 30° C. the mixture is added to the suspended diazonium salt. 3,3,3-trifluoropropene (molar ratio diazonium salt to 3,3,3-trifluoropropene 1:1.01) is introduced during 5 hours and stirring is continued until no diazonium salt can be detected. The suspension is then ready for hydrogenation.

b) Preparation of sodium-[2-(3,3,3-trifluoro-prop-1-yl)]-benzene-sulfonate

Charcoal (weight ratio sodium-[2-(3,3,3-trifluoro-1-propenyl)]-benzene-sulfonate to charcoal 10:1) is added to the above suspension and hydrogen is introduced during 6 hours at 35° to 40° C. and a pressure of 1 bar. Suspended material is filtered off and the pentanol solution is washed with water/sodium hydroxide to remove sodium acetate and byproducts. Pentanole is partially distilled off, water is added and the remaining pentanole is removed by azeotropic distillation. The resulting solution of the product in water is used in the next step.

c) Preparation of 2-(3,3,3-trifluoro-prop-1-yl)]-benzene-sulfonamide

Water is distilled off from the above solution. Chlorobenzene is added and the remaining water is removed by azeotropic distillation. Phosgene (molar ratio of sodium-[2-(3,3,3-trifluoro-prop-1-yl)]-benzene-sulfonate to phosgene 1:2.5) is introduced at 85° to 105° C. during 5 hours in the presence of catalytic amounts of dimethylformamide (molar ratio phosgene to dimethylformamide 1:0.1). The solution is then treated with an excess of aqueous $NH_3$ (content 30%, molar ratio 2-(3,3,3-trifluoro-prop-1-yl)-benzene-sulfochloride to $NH_3$ 1:4) at 60° C. during 1 hour and the reaction mixture is stirred for further 2 hours. After cooling the precipitated is filtered off and used in the next step.

d) Preparation of N-(4-methoxy-6-methyl-1,3,5-tiazine-2-yl)-N'-[2-(3,3,3-trifluoroprop-1-yl)-benzenesulfonyl]-urea The product of the previous step is suspended in hot chlorobenzene. In the presence of catalytic amounts of cyclohexylisocyanate (molar ratio of product to cyclohexylisocyanate 1:0.01) phosgene (molar ratio of product to phosgene 1:3) is introduced at 100° to 120° C. during 5 hours. The chlorobenzene is distilled off until a concentration of 25% isocyanate is reached. This solution is added during 1 hour to a suspension of 2-amino-4-methyl-6-methoxy-triazine in chlorobenzene at 90° C. The suspension is stirred for further 90 minutes and then cooled. The product is filtered off and vacuum dried. 170 kg of pure product are prepared at the pilot plant.

We claim:

1. A process for the manufacture of compounds of the formula V

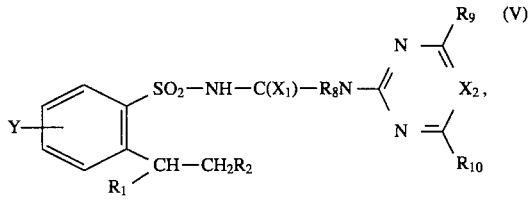

wherein $X_1$ is S or O, $X_2$ is N or CH,

Y is H, Cl, F or Br, $R_1$ is H, F, Cl, Br or —COOR$_3$, $R_2$ is —COO($C_1$–$C_4$-alkyl), —(CO)R$_3$ or $C_1$–$C_2$-alkyl which is unsubstituted or substituted by halogen atoms, and $R_3$ is H or $C_1$–$C_4$-alkyl, $R_8$ is H, $C_1$–$C_3$alkyl or $C_1$–$C_3$alkoxy $R_9$ is $C_1$–$C_3$alkyl, $C_1$–$C_3$haloalkyl, $C_1$–$C_3$alkoxy or $C_1$–$C_3$haloalkoxy, and $R_{10}$ is H, halogen, $NH_2$, NH($C_1$–$C_3$alkyl), NH($C_1$–$C_3$alkyl)$_2$, $C_1$–$C_3$alkyl, $C_1$–$C_3$haloalkyl, $C_1$–$C_3$alkoxy or $C_1$–$C_3$haloalkoxy, by a) reacting in a first step 1 mole equivalent of a compound of the formula IIb

wherein $X_3$ represents hydroxyl, —OM or —O$(M_1)_{1/2}$, where M is an alkali metal atom or a tertiary ammonium group, having from 3 to 18 carbon atoms, and $M_1$ is an alkaline earth metal atom, with at least 1 mole equivalent of a compound of formula IIIb $$CHR_1=CHR_2 \quad \text{(IIIb),}$$

optionally in the presence of an inert solvent, and in the presence of a catalytic amount of a homogeneous palladium catalyst and a base selected from alkali metal salts, alkaline earth metal salts and a tertiary ammonium salt of a carboxylic acid to give a compound of the formula IVb

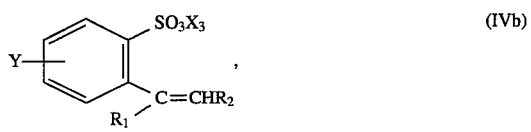

and b) hydrogenating in a second step the compound of the formula IVb optionally in the presence of an inert solvent and in the presence of catalytic amounts of a hydrogenation catalyst, to form a compound of the formula Ib

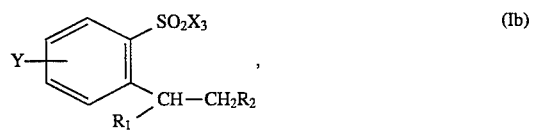

c) reacting in a third step the compound of formula Ib with at least 1 mole of a halogenating agent to form the sulfochloride, which is then reacted with $NH_3$ to give the sulfonamide of the formula Ic

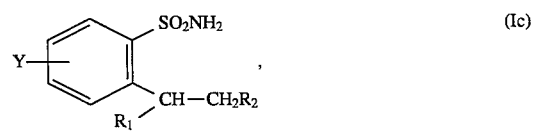

d) reacting the compound of the formula Ic with $COCl_2$ or $CSCl_2$ to obtain a compound of the formula VI

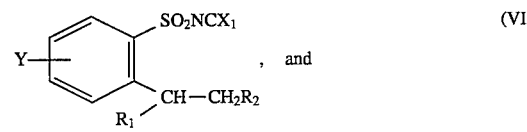, and e) reacting the compound of the formula VI with a compound of the formula VII

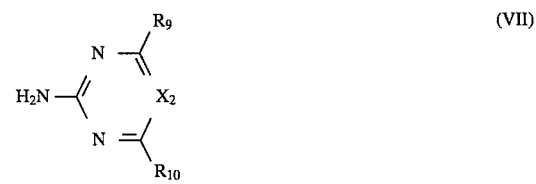

to form the compound of the formula V, characterised in that the homogeneous palladium catalyst is reduced to insoluble palladium metal in the step a) reaction mixture, which is subsequently used as the heterogeneous hydrogenation catalyst.

2. A process according to claim 1, characterised in that the heterogeneous palladium hydrogenation catalyst in the step b) reaction is formed in situ from the homogeneous palladium catalyst in the obtained step a) reaction mixture in starting the hydrogenation by introducing hydrogen.

3. A process according to claim 1, wherein a solid palladium support material for the heterogeneous hydrogenation catalyst is added prior to the start of the hydrogenation.

4. A process according to claim 1, wherein $X_3$ represents hydroxyl or a group —OM, wherein M is an alkali metal.

5. A process according to claim 1, wherein $X_3$ represents the group —ONa.

6. A process according to claim 1, wherein $X_1$ is O.

7. A process according to claim 1, wherein $X_2$ is N.

8. A process according to claim 1, wherein $R_8$ is H.

9. A process according to claim 1, wherein $R_9$ is $C_1$–$C_3$alkyl.

10. A process according to claim 9, wherein $R_9$ is methyl or ethyl.

11. A process according to claim 1, wherein $R_{10}$ is $C_1$–$C_3$alkyl or $C_1$–$C_3$alkoxy.

12. A process according to claim 11, wherein $R_{10}$ is methyl, ethyl, methoxy or ethoxy.

13. A process according to claim 1 for the production of N-(4-methoxy-6-methyl-1,3,5-triazine- 2-yl)-N'-[2-(3,3,3-trifluoroprop-1-yl)-benzenesulfonyl]-urea.

14. A process according to claim 1, wherein in the step c) reaction the halogenating agent is $COCl_2$.

15. A process according to claim 14, wherein the reaction is catalyzed by the addition of dimethylformamide.

16. A process according to claim 15, wherein 0.001 to 10 mole percent of dimethylformamide are used related to the amount of compound Ib.

17. A process according to claim 14, wherein the reaction temperature is from 20° to 150° C.

18. A process according to claim 14, wherein chlorobenzene is used as solvent.

19. A process according to claim 14, wherein the sulfochloride is treated without isolation in the obtained reaction mixture with aqueous $NH_3$ to form the sulfonamide of formula Ic.

20. A process according to claim 19, wherein the reaction temperature is from 20° to 100° C.

21. A process according to claim 1, wherein the step d) reaction is carried out with an excess of phosgene or thiophosgene.

22. A process according to claim 21, wherein the reaction temperature is from 50° to 180° C.

23. A process according to claim 21, wherein the reaction is catalyzed by the addition of aliphatic or cycloaliphatic isocyanates having 1 to 10 carbon atoms.

24. A process according to claim 23, wherein cyclohexylisocyanate is used as catalyst.

25. A process according to claim 23, wherein 0.001 to 10 mole percent catalyst are used related to the amount of compound Ic.

26. A process according to claim 21, Wherein chlorobenzene is used as solvent.

27. A process according to claim 1, wherein the step e) reaction is carried out in the presence of chlorobenzene as solvent.

28. A process according to claim 1, wherein the step e) reaction is carded out at a temperature range from 20° to 180° C.

29. A process according to claim 1, wherein the step e) reaction is carded out under normal pressure or an elevated pressure of up to 1 bar.

30. A process according to claim 1, wherein the step e) reaction is carded out in adding the obtained reaction solution with the isocyanate of formula VI to the solution or suspension of the compound of the formula VII.

* * * * *